United States Patent [19]

Gross

[11] Patent Number: 5,002,872

[45] Date of Patent: Mar. 26, 1991

[54] ENZYME MEDIATED COUPLING REACTIONS

[75] Inventor: Akiva T. Gross, Newton, Mass.

[73] Assignee: W. R. Grace & Co.-Conn., New York, N.Y.

[21] Appl. No.: 349,688

[22] Filed: May 10, 1989

[51] Int. Cl.$^5$ .......................... C12P 21/00; C12R 1/63
[52] U.S. Cl. .................................. 435/68.1; 435/71.1; 435/71.2; 435/212; 435/219; 435/220; 435/909
[58] Field of Search ...................... 435/219, 220, 71.1, 435/71.2, 68.1, 212, 909

[56] References Cited

U.S. PATENT DOCUMENTS

| | | | |
|---|---|---|---|
| 3,972,773 | 8/1976 | Isowa et al. | 435/70 |
| 4,086,136 | 4/1978 | Isowa et al. | 435/70 |
| 4,116,768 | 9/1978 | Isowa et al. | 435/70 |
| 4,119,493 | 10/1978 | Isowa et al. | 435/70 |
| 4,165,311 | 8/1979 | Isowa et al. | 560/13 |
| 4,256,836 | 3/1981 | Isowa et al. | 435/70 |
| 4,284,721 | 8/1981 | Oyama et al. | 435/70 |
| 4,293,648 | 10/1981 | Davino | 435/70 |
| 4,339,534 | 7/1982 | Johansen et al. | 435/70 |
| 4,436,925 | 3/1984 | Isowa et al. | 560/19 |
| 4,521,514 | 6/1985 | Oyama et al. | 435/70 |
| 4,572,894 | 2/1986 | Imahori et al. | |

FOREIGN PATENT DOCUMENTS

| | | |
|---|---|---|
| 82928/87 | 6/1988 | Australia . |
| 0272564 | 6/1988 | European Pat. Off. . |
| 169993 | 7/1988 | Japan . |
| 1523546 | 9/1978 | United Kingdom . |
| 1533129 | 11/1978 | United Kingdom . |

OTHER PUBLICATIONS

Biotech Derwent Abs. 89-02943 Reslow et al., EJBCAI Eur. J. Biochem (1988) 177, 2, 313-318.
Biotech Derwent Abs. 85-179237/30 Likos et al., EP-149594, Jul. 1985.
Biotech Abs. Derwent 89-14093 Coccak Collect Czech Chem. Commun. (1989) 54, 7, 2027-41 Cerovsky et al. Elphinoff-Felkin; "Synthesis of erythro-Beta--phenylserine", 232/241-43, 1951.
Chang et al.; "The Hydrogenation of Alpha-Oximino Ketones"; J. Am. Chem. Soc., vol. 75, pp. 89-91; 1951.
Jones et al.; "Asymmetric Synthesis and Resolutions Using Enzymes"; Appl. Biolchem. Sys., p. 107; 1953.
Isowa et al.; "Peptide Synthesis with Proteinases, Fragment Condensation of ZleuGlnGlyOH or ZGlnGlyOH with HLeuValNH$_2$, Using Metalloproteinases"; Bull. Chem. Soc., vol. 51, pp. 271-276; 1978.

Inouye et al.; "Enzyme Assisted Semisynthesis of Human Insulin"; J. Am. Chem. Soc., pp. 751-752; 1979.
Jones et al.; "Effects of Organic Cosolvents on enzyme stereospecificity, The Enantiomeric specificity of alpha-chymotrypsin is Reduced by High Organic Solvent Concentrations"; Can. J. Chem., vol. 57, p. 2245, 1979.
Kullman; "Proteases as Catalysts for Enzymatic Synthesis of Opioid Peptides"; J. Biol. Chem.; vol. 255/8234-38; 1980.
Kullman; "Protease-Mediated Peptide Bond Formation"; J. Biol. Chem.; vol. 256/1301-04; 1981.
Konnecke et al.; "Peptide Synthesis by Means of Immobilized Enzymes"; Monatschrifts Fur Chemie; vol. 112/469-81; 1981.
Wayne et al.; "Thermolysin-Catalyzed Peptide Bond Synthesis"; Proc. Nat. Acad. Sci., vol. 80/3241; 1983.
Nilsson et al.; Biotech. Bioeng., vol. 26/1146; 1984 "Peptide Synthesis in Aqueous-Organic Solvent Mixtures with alpha-Chymotrypsin Immobilized to Tresyl Chloride-Activated Agarose".
Cerovosky et al., "Enzymatically Catalyzed Synthesis of Dipeptides of -carboxy-L-Glutamic Acid from Benzyloxycarbonyl-y-Carboxy-DL-Glutamic-Acid"; Coll. Czechos. Chem., vol. 49/231, 1984.
Ooshima et al.; "Synthesis of Aspartame Precursor by Solid Thermolysin In Organic Solvent"; Biotech. Lett.; vol. 7/789, 1985.
Jakubke et al.; "Basic Principles of Protease-Catalysed Peptide Bond Formation"; Angew, Chem., vol. 24/85, 1985.
West et al.; "Enzyme-Catalyzed Irreversible Formation of Peptides Containing D-Amino Acids"; J. Org. Chem., vol. 51/2728, 1986.
Klibanov et al.; "Enzymes that Work in Organic Solvents"; Chemtech., p. 354, 1986.
U.S. Application 789,593-Chmurny et al.
U.S. Application 789,595-Chmurny et al.
Oyama, "Biocat.-Org. Media", pp. 209-224, 1987.
Rodgers et al., "Biocat.-Org. Media", pp. 405-409, 1987.

*Primary Examiner*—Herbert J. Lilling
*Attorney, Agent, or Firm*—Vanessa L. Appleby; Jill H. Krafte; Steven T. Trinker

[57] ABSTRACT

Disclosed herein is an enzymatic process to bind two amino acids in the presence of a water-miscible solvent. Preferably the amino acids are precursors of aspartame and a preferred solvent is acetonitrile.

22 Claims, No Drawings

ENZYME MEDIATED COUPLING REACTIONS

BACKGROUND OF THE INVENTION

Enzyme mediated synthesis of dipeptides is well known. Thus U.S. Pat. Nos. 4,165,311; 4,436,925 and 4,256,836 describe synthesis in aqueous medium to form insoluble addition compounds, e.g., the addition compound of one mol of phenylalanine methyl ester with one mol of N-protected aspartyl-phenylalanine methyl ester. U.S. Pat. No. 4,284,721 teaches that N-protected aspartic acid and phenylalanine lower alkyl esters can be enzymatically coupled in the presence of a water-immiscible solvent which can contain water-miscible co-solvents, but the amount of the water-miscible solvent must be limited to avoid inactivating or inhibiting the enzyme U.S. Pat. Nos. 4,116,768 and 4,119,493 contain similar teachings with regard to the use of water-miscible solvents as co-solvents in aqueous medium. Similarly *Angew. Chem. Int. Ed. Engl.* 24 (1985) Number 2, page 87, indicates that water-miscible solvents can be used as co-solvents in admixture with water but that the catalytic activity of protease enzymes decreases as the concentration of the co-solvent increases and that at 50% and above no synthesis occurs where chymotrypsin is used as the enzyme. As a possible exception, the use of a polyol (e.g., 1,4-butanediol) may in some cases stabilize the enzyme.

The use of aqueous or aqueous-organic media for enzymatic coupling to form N-formyl dipeptides (e.g., N-formyl aspartame) and polypeptides is also described in WO 8604924 and European Patent Publication 0149594.

A number of articles in various scientific journals also discuss the use of enzymes with a combination of water and water-miscible organic solvents and obtain yields which appear to vary depending upon the choice of solvent, amount of water, enzyme and substrate. Also, whether the enzyme is immobilized appears to be a factor. The use of a 50/50 acetonitrile/water solvent system is described by Nilsson and Mosbach in *Biotech Bioeng.* 26, 1146 (1984). This reference also describes the use of butanediol/water (90/10). The use of acetonitrile as a solvent is also discussed by J.B. Jones, and J.F. Beck, in *Applications of Biochemical Systems in Organic Chemistry*, Part 1 (J.B. Jones, C.J. Sih. and D. Perlman, eds.) p. 107 ff. New York; J. Wiley, 1976; and J.B. Jones and M.M. Mehes., *Can. J. Chem.* 57, 2245 (1979). The coupling of L-phenylalanine methyl ester (i.e., L-pheOMe) and N-protected N-carbobenzyloxy-aspartic acid (i.e., Z-asp) using a mixture of water-immiscible/water miscible solvents is described in *Biotech. Lett.* 7, 789 (1985). Konnecke et al. in *Monatshrifts fur Chemie*, 112, 469–481 (1981) at page 475 refer to the use of acetonitrile as a solvent. Other articles of interest are *J. Biochem.*, 89, 385 (1981); *J. Org. Chem.*, 51, 2728(1986); *Coll Czechos. Chem. Comm.*, 49, 31 (1984); and *Proc. Natl. Acad. Sci.*, 80, 3241 (1983).

While the literature indicates that enzymes in general and proteases in particular have been employed in both water-miscible and water-immiscible organic solvents, there appears to be a general conception that the water-miscible solvents are somewhat inferior. Thus it has been said that "most enzymes are inactive in hydrophilic, water-miscible organic solvents, which is easy to understand in terms of partitioning of the essential water from the enzyme into them." (A.M. Klibanov, *Chemtech*, page 354, June 1986).

This invention is based on the use of proteases in water-miscible organic solvents.

DESCRIPTION OF THE INVENTION

The invention is a process wherein an enzyme is used to catalyze peptide bond formation between two substrates selected from the group consisting of N-substituted aspartic acid and a phenylalanine lower alkyl ester. The benzylic carbon atom of the ester can be substituted with one or more labile groups readily replaceable with hydrogen. The process of the invention encompasses carrying out the above process in the presence of a water-miscible organic solvent.

The use of water-miscible solvents offers many advantages. Contrary to expectations the solvent can be employed without depleting the enzyme of essential water. For example in conducting a continuous process the amount of water essential for enzyme activity can be provided by maintaining from 2–10% by weight of the solvent system of water with the balance being the water-miscible solvent or a mixture thereof with other solvents. In a closed system (e.g., essentially a batch reaction as opposed to a continuous reaction) the enzyme and its support will lose enough water to provide the 2–10% by weight referred to above. It should be understood however that if the enzyme is contacted with a sufficiently large amount of essentially anhydrous water-miscible solvent, enough water will be extracted so that the water level in the solvent falls below about 2% and the enzyme is denatured. Amounts of water in excess of 10%, e.g., as high as 50%, can be employed but in doing so the advantages of using the water-miscible solvent may be reduced.

In many reactions the use of a water-miscible solvent as the sole solvent or as a co-solvent can provide a single liquid phase, thereby avoiding phase transfer limitations which arise where the solvent is immiscible with water. For example, use of a water-miscible solvent will frequently increase the reaction rate. Also the dielectric constant of most useful water-miscible organic solvents is from 5 to 60 (preferably 30 to 60) which contributes to formation of a single liquid phase because most amino acid derivatives are relatively polar and are soluble in such solvents. For example the methyl ester of phenylalanine is much more soluble in acetonitrile than in hexane or ethyl acetate.

The use of a water-miscible solvent can also shift the reaction equilibrium. For example, in ethyl acetate the reaction of N-formyl aspartic acid with phenylalanine methyl ester gives a yield of about 10%, but the yield is about 80% in acetonitrile.

The enzyme, whether immobilized or in "free" form, may be much more stable in water-miscible solvent as opposed to a water-immiscible solvent. For example, thermolysin immobilized on silica or an ion exchange resin (e.g., Amberlite) is more stable in acetonitrile than in ethyl acetate. By "stability" it is meant that the enzyme resists denaturation whether by extraction of water or other means. Also the term "solvent system" is used to designate the solvent portion of the liquid phase, and includes the water-miscible solvent and any co-solvents utilized therewith, e.g., water or a water-miscible solvent.

By the term "water-miscible organic solvent" is meant those organic liquids which are miscible with water in any proportion to form a single phase system.

Examples of suitable organic solvents include alcohols (e.g., ethanol, 1-propanol, and 2-propanol); polyols (e.g., 1,4-butanediol, and diethylene glycol); nitriles (e.g., acetonitrile); and ethers (e.g., dioxane and tetrahydrofuran); as well as other solvents such as dimethylformamide, dimethyl sulfoxide, and acetone.

Acetonitrile is a preferred water-miscible solvent. A further embodiment of the invention is that acetonitrile can be used with a wide variety of amino acids and enzymes to form dipeptides and polypeptides by an enzyme mediated coupling reaction. Examples of suitable amino acids for use in this reaction include aliphatic amino acids such as monoamino monocarboxylic acids, e.g., glycine (Gly), alanine (Ala), valine (Val), norvaline (nor-Val), leucine (Leu), isoleucine (iso-Leu), norleucine (nor-Leu); oxyamino acids, e.g., serine (Ser), threonine (Thr), homo-serine (homo-Ser); sulfur-containing amino acids, e.g., methionine (Met) or cystine (CysS) and cysteine (CysH); monoamino dicarboxylic acids, e.g., aspartic acid (Asp) and glutamic acid (Glu); diamino monocarboxylic acids, e.g., ornithine (Orn), lysine (Lys), arginine (Arg); aromatic amino acids, e.g., phenylalanine (Phe), tyrosine (Tyr) and heterocyclic amino acids, e.g., histidine (His), tryptophan (Trp). (The amino acids are designated by symbols which are commonly used in the field.)

Care should be used in solvent selection. For example, if the enzyme contains a metal, the solvent should not complex the metal. DMF and DMSO appear to complex the metal component in metalloproteinases and should preferably be restricted to 50% or less (on a molar basis) of the solvent system, e.g., the balance can be water or another solvent. The solvent should also be inert in the sense that it does not chemically react with the enzyme or the substrates. For example, if acetone is the solvent, it should be used under conditions which minimize reaction with the amine groups of a substrate or an enzyme.

The amino acids functioning as the acyl donor generally have a protective group at the N position. Examples of suitable N-protective groups are those normally used in peptide synthesis such as tertiary alkoxycarbonyl groups, e.g., t-butyloxylcarbonyl (BOC-), t-amyloxycarbonyl (t-Aoc); benzyloxycarbonyl groups which can be substituted with an inert substituent, such as benzyloxycarbonyl (Z-), p-methoxybenzyloxycarbonyl (PMZ-), 3,5-dimethoxybenzyloxycarbonyl (Z(O-Me)$_2$-), 2,4,6-trimethylbenzyloxycarbonyl (TMZ-), p-phenylazobenzyloxycarbonyl (PZ-), p-toluenesulfonyl (tosyl-); o-nitrophenyl sulfenyl (Nps-), and the like. Also formyl can be employed.

Examples of suitable amino acids for donating the amino moiety in formation of a dipeptide or polypeptide include any of those set forth above. Phenylalanine is preferred, and particularly derivatives substituted at the benzylic carbon can be employed, e.g., derivatives wherein the benzylic carbon is substituted with at least one group easily replaceable by methods such as catalytic hydrogenolysis or electrochemical reductive cleavage. Examples of suitable substituted phenylalanine derivatives include those corresponding to the formula:

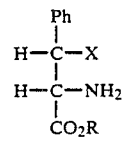

wherein Ph is phenyl (substituted or unsubstituted), while X is —OH, —SH, —Cl, —Br, —I, —OCOCH$_3$, —OCOOCH$_3$, —NH$_2$ or —SCH$_3$ and R is a lower alkyl group having from 1 to 4 carbon atoms.

The amino-donating amino acids are protected by suitable C-terminal protective groups. The protective groups for the carboxyl group (C-terminal protective groups) of the amine component include alkoxy groups such as methoxy (—OMe), ethoxy (—OEt); tertiary alkoxy groups such as t-butoxy (—O—t—Bu); and benzyloxy groups which can be substituted such as benzyloxy (—OBzl), p-nitrobenzyloxy (—OBzl(p—NO$_2$)), benzhydryloxy (—OBzh), benzylamino (—NHBzl), 2,4-dimethoxybenzylamino (—NHDMB), benzhydrylamino (—NHBzh) or unsubstituted amino (—NH$_2$), etc. Also the amide and hydrazide groups can be employed as C-terminal protective groups.

Enzymes which can be employed are those known to mediate peptide bond formation and include aminopeptidases (e.g., leucine aminopeptidase), carboxypeptidases (e.g., carboxypeptidase y), serine proteinases (e.g., chymotrypsin, subtilisin), thiol proteinases (e.g., papain, bromelain), acid proteinases (e.g., pepsin), and metalloproteinases (e.g., thermolysin, and metalloendoproteinase from *Vibrio Proteolyticus* (see Example 6). The enzyme need not be used in purified form but may be a more or less crude preparation (e.g., a concentrated partially purified fermentation broth) containing an enzyme or a plurality of enzymes.

It should be understood that the water-miscible organic solvents can be utilized either in essentially anhydrous "neat" form or in conjunction with water and/or other organic solvents (both water-immiscible and water-miscible solvents). Where water is employed, the amount should generally be less than 50% by weight based on the total solvent system (e.g., water plus water-miscible solvent). However, certain solvents appear to complex metal ions and thereby inactivate various metalloproteinase enzymes, and the amount of water used with such solvents should equal or exceed 50% by weight of the solvent system. Examples of complexing solvents include DMF and DMSO. If the solvent is in dry or neat form, it will contain some water (e.g., up to about 10% by weight of the solvent) which has been given up by the support used to immobilize the enzyme. For the preferred acetonitrile solvent, generally the amount of water is kept at a minimum and "neat" acetonitrile has been found to be a good solvent, in which case the only water provided will be that coming from the support. However when run on a continuous basis the water level in the acetonitrile solvent should be maintained at a level of at least 10 weight % and generally will fall within the range of from 5 to 50 weight %. This amount of water is advisable to avoid dehydrating the enzyme and can be of assistance in dissolving substrates. If desired, the water can be added via the substrate stream if the process is practiced on a continuous basis. Specifically in coupling N-protected-aspartic acid with phenylalanine lower alkyl esters and benzyl substituted derivatives thereof (whether via a batch or continuous process), the acetonitrile can also be used with varying amounts of water, but it is preferred that the amount of water be less than 50 weight percent, i.e., by weight the $CH_3CN/H_2O$ ratio should exceed 1, and preferably should exceed about 2.5.

Using procedures known to those skilled in the art, the organic solvent selected for each coupling reaction can be optimized in view of a number of factors such as the solubility of the substrates and dipeptide or polypeptide product in the solvent, the amount of water or other co-solvent present, the effect of the co-solvent upon the enzyme and other factors.

As is well known many protease enzymes also exhibit esterase activity. This activity can be decreased on occasion by appropriate selection of the organic water-miscible solvent. For example acetonitrile has exhibited some effect in reducing esterase activity. Also it is possible to use an inhibitor to further decrease esterase activity if the esterase activity is contributed by a separate protein or if the site for esterase activity differs from the protease site, assuming both sites are on the same molecule. Suitable inhibitors can be extracted from oats, fava, kidney beans and potato. The method of extraction is disclosed in Nippon Nogei Kogaku Kaishi, 31, page 38(1957). The inhibitor need not be a pure material, but can be a crude extract.

By the term "bound" it is meant that the enzyme is immobilized on a suitable insoluble carrier to form a complex which can be recovered and reused. Suitable methods of immobilization include physical adsorption, ionic bonding, covalent bonding, crosslinking following adsorption or other methods of inclusion of the enzyme in or on a supporting material essentially insoluble in the reaction medium. Suitable substrates include siliceous materials (e.g., porous silica), non-silicious ceramics (e.g., alumina), or natural or synthetic organic polymeric materials (e.g., resins such as Amberlite XAD-7, polyacrylamide copolymers, agarose, and alginates). By contrast a "free" enzyme is unbound and can be either dissolved or suspended in the solvent system.

It is preferable to have a high concentration of the substrate amino acids to enable the process to be carried out at a reasonable reaction rate. Each substrate for the coupling reaction is used in a concentration within the solubility thereof in the solvent. However, since the materials are consumed as the reaction proceeds, it is possible to have a portion of any substrate in a suspended state. In solution the substrate materials should each be present in a concentration ranging from about 0.001 M and to about 2 M, and preferably between about 0.1 M and about 1 M.

With regard to the N-substituted aspartic acid/phenylalanine lower alkyl ester coupling reaction, the acid/ester mole ratio can be 1:1 in mol ratio when both substrates are in L configuration. Practically, they may be used in a ratio ranging between 10:1 and 1:10 and preferably between 3:1 and 1:5. In cases where the materials are in a DL configuration, they may be used in quantities which result in a ratio of the L-isomers as described above.

The invention can be carried out, for example, by allowing a water-containing immobilized enzyme to be suspended in the organic solvent miscible with water which also contains both of the starting materials and then by allowing the reaction to proceed with stirring. Upon completion of the reaction, the immobilized enzyme and a suspension or solution containing a reaction product can be separated from each other by subjecting the product-containing medium to filtration or other separation processes.

The invention can also be carried out in a column filled with the water-containing immobilized enzyme, by allowing the water-miscible organic solvent which contains the two starting materials to flow through the column. This process permits the reaction to be continuously carried out and is advantageous for an industrial application of the invention.

The reaction temperature is usually in the range between about 10° and about 80° C. and preferably between about 20° and about 50° C.

The reaction time depends on the concentrations of the two substrates, the quantity of the immobilized enzyme, a predetermined conversion rate, etc. However, usually the reaction time of about 0.5 to about 200 hours and preferably about 2 to about 24 hours suffices.

Where the desired product is the dipeptide known as aspartame, the reaction product, i.e., N-substituted-L-aspartyl-L-phenylalanine methyl ester can be isolated by conventional means such as concentrating the reaction mixture followed by crystallization, extraction or the like. The reaction mixture can also be separated from the immobilized enzyme by suitable processes well known in the art. Following separation the immobilized enzyme can be reused.

In carrying out the invention, the amino acid substrates may be in the DL or the L configuration. Where the enzyme is specific for L isomers, if DL isomers are employed, only the L isomer participates in the reaction, while the D isomer remains unreacted in the reaction medium. If the enzyme has no stereospecific preference, the D isomer can be used, e.g., with enzymes such as serine proteases which have no D,L specificity, the amino donor (e.g., alanine or phenylalanine) can be D.

EXAMPLE 1

Immobilization of Thermoase

Amberlite XAD-7 resin beads were washed with ethanol and then with water to remove fines. The washed beads were re-suspended in 0.05 M MES-0.02 M $CaCl_2$ solution. After removing excess water by filtering Amberlite XAD-7 through vacuum, beads (100 grams) were suspended in 100 ml of 0.05 M MES-0.02 M $CaCl_2$ buffer containing 9 grams Thermoase at 4° C. After shaking overnight, the immobilized Thermoase was thoroughly washed with the coupling buffer and then was vacuum filtered.

EXAMPLE 2

Coupling In "Neat" Water-Miscible Solvents Using Free Enzyme

In a 25 ml flask, Z-L-aspartic acid (0.192 g, 80 mM) and D,L-erythro - phenylserine methyl ester (0.42 g, 240 mM) were dissolved in neat organic solvent (Acetonitrile, Dioxane, THF or DMF) to give a final volume of 9 ml. Crude Thermoase powder (120 mg) was added to the above described reaction mixture and the reaction flask was shaken at 40° C. After 10 hours, concentration of Z-aspartyl-L-erythro-phenylserine methyl ester (Z-OH-aspartame) in the reaction mixture was determined by HPLC. Results are shown in the following table.

| Solvent | THF | DMF | Dioxane | Acetonitrile |
| --- | --- | --- | --- | --- |
| Concentration | 1.1 mM | 0 | 1.2 mM | 1.5 mM |

| Solvent | THF | DMF | Dioxane | Acetonitrile |
|---|---|---|---|---|
| of Z—OH-aspartame | | | | 5 |

EXAMPLE 3
Coupling Using Immobilized Enzyme

The same experiment described in Example 2 was repeated except that 1 g of immobilized Thermoase (the immobilization of Thermoase was described in Example 1) was used to replace 120 mg of crude Thermoase powder. After 20 hours' reaction, the concentration of Z-OH-aspartame was determined by HPLC. Results are shown in the following Table.

| Solvent | THF | DMF | Dioxane | Acetonitrile |
|---|---|---|---|---|
| Concentration of Z—OH-aspartame | 8.1 mM | 0.5 mM | 9.9 mM | 65 mM |

EXAMPLE 4
Coupling in Acetonitrile To Form Z-Phe-PheOMe Dipeptide

In a 25 mil flask, Z-L-phenylalanine (0.216 g, 80 mM, and L-phenylalanine methyl ester (0.32 g, 200 mM0 were dissolved in neat acetonitrile to give a final volume of 9 ml. Immobilized Thermoase (2.5 g) was added to the reaction mixture and the flask was shaken at 40° C. After 18 hours reaction, the concentration of Z-L-phenylalanyl-L-phenylalanine methyl ester was determined to be 70 mM.

EXAMPLE 5
Coupling of D,L-Erythro-phenylserine

In a 1 liter bioreactor, 30 g Z-asp, 65 g D,L-erythrophenylserine methyl ester and 80 g of wet immobilized Thermoase were mixed in 650 ml acetonitrile at 40° C. After 24 hours, 22 g of Z-L-Aspartyl-phenylserine methyl ester was produced.

EXAMPLE 6
Preparation of Protease (i.e., "Vibrio") by Fermentation of Vibrio Proteolyticus 1. Preparation of Seed Culture
    A. Preparation—100 ml. seed medium is contained in a 500 ml. indented Erlenmeyer flask and autoclaved 20 minutes at 121° C.
    B. Inoculation—A single −70° C. ampoule of organism is thawed under tap water, then aseptically transferred to the seed flask.
    C. Incubation—The inoculated flask is incubated 18 hours at 250 rpm/27° C.
    D. Growth measured at 640 nm. is between an optical density of 4.0 to 6.0; broth pH is approximately 8.0.
2. Enlarged Fermentation—1.0-liter volume in a 1.5-liter fermenter.
    A. Preparation—All medium ingredients are added to the vessel (polypeptone—20 gm., sea salts—20 gm., $MgSO_4 7 H_2O$—0.4 gm., P-2000—0.2 ml.) and pH is unadjusted prior to sterilization; it should be nearly pH 7.0. A 1.0-liter vessel, if sterilized in an autoclave, should be sterilized 45 min. at a temperature of 121° C.
    B. Inoculation
        (1) First set and double check operating parameters:
            a. pH to 8.6 with 6N NaOH
            b. temperature=27° C.
            c. RPM=1000
            d. dissolved oxygen readout to 100% at 1.0-LPM air.
        (2) Inoculate with 10 ml. seed broth.
    C. Operation
        (1) Maintain aforementioned parameters.
        (2) Dissolved oxygen will drop to about 75-80% at peak demand.
        (3) Monitor the following:
            a. Optical Density - read at 640nm Absorbance. Peaks at about 10-12 O.D. in about 12-14 hours.
            b. Production of metalloendopeptidase—to about 0.1 units/sec.
3. Harvest and Concentration of VIBRIO Enzyme
    At about 14-16 hours into the fermentation the product enzyme reaches titers of approximately 0.10 units/sec. activity as measured by the FAGLA assay. The broth is harvested before the cells lyse to an advanced stage (about 10-25%).
    First, the whole broth is centrifuged to separate the cell portion. Then the supernatant is concentrated 70-100 fold, utilizing an Amicon SIOYIO and SIYIO ultrafilter cartridges. Finally the concentrate is washed three times with 0.01 M HEPES plus 0.01 M $CaCl_2$ (pH-7.2) buffer solution.
    A culture of *Vibrio proteolyticus* using the procedure described above has been deposited with the American Type Culture Collection, 12301 Park Lawn Drive, Rockville, Md. 20852, under No. ATCC 53559.

EXAMPLE 5
Coupling of N-Formyl-Aspartic Acid

Fermentation broth from *Vibrio Proteolyticus*, produced as in Example 6, was concentrated and washed. The neutral protease in the fermentation broth was immobilized on Amberlite XAD-7 in a manner similar to Example 1. N-Formyl-Aspartic acid (1.93 g) and L-phenylalanine methyl ester (6.2 g) were dissolved in acetonitrile to give a final volume of 150 ml. After the addition of 14.5 g wet immobilized neutral protease, the reaction was run for 24 hours at room temperature. The final product concentration (N-formyl-aspartyl- L-phenylalanine methyl ester) was 11.7 g/l determined by HPLC. The solvent was evaporated in vacuum and the residue dissolved in ethylacetate and washed twice with 1N HCl. The aqueous phase was treated with acetate. The combined organic phase was washed with brine and dried over anhydrous $MgSO_4$. Evaporation of the solvent afforded a colorless solid that was crystallized from dichloroethane and identified as N-formyl-aspartame.

EXAMPLE 8
Use of Water/Water-miscible Solvent Systems

Water/water-miscible organic solvents were evaluated as organic media for enzymatic dipeptide synthesis reactions. Substrate concentrations in each reaction mixture were 80 mM Z-aspartic acid and 240 mM D,L-erythro-phenylserine methyl ester. The immobilized catalyst using Thermoase enzyme and silica was prepared by the covalent carbonyl-alkylamine coupling method of Weetall[1].

1. Weetall, H.H., 1976. *Methods in Enzymology*, v. 64, pp. 134–148.

Z-aspartyl-L-erythro-phenylserine methyl ester synthesis was not observed in concentrations of ethanol, dimethyl sulfoxide, N,N-dimethylformamide, or acetone which were greater than 90% solvent when silica immobilized enzyme was used. Dipeptide yields in neat 1,2-dimethoxyethane, and 1,4-butanediol when using silica immobilized enzyme were both 25% of the theoretical yield. This result should be compared with Example 3 when Amberlite was employed rather than silica and demonstrates that the choice of carrier can effect the enzymatic reaction. Dipeptide yields in 95% ethanol and 1,4-butanediol when using the Amberlite immobilized enzyme were 20% and 40%, respectively. All reactions were incubated at 40° C.

EXAMPLE 9

Use of Water/Acetonitrile Solvent Systems

Acetonitrile was evaluated as a water/water-miscible organic medium for enzymatic dipeptide synthesis using either immobilized or unbound Thermoase enzyme. The substrate concentrations used in the synthesis reaction were 80 mM Z-aspartic acid and 240 mM of either D,L-erythro-phenylserine methyl ester or L-phenylalanine methyl ester. Thermoase enzyme was immobilized on Amberlite resin by adsorption as described in Example 1. Synthesis reactions were evaluated in 100% acetonitrile, 75% acetonitrile—25% water, 50% acetonitrile—50% water, and 25% acetonitrile—75% water. Reactions were monitored for a period of 24 hours to determine reaction rates and yields. Low dipeptide synthesis rates were observed when unbound enzyme was used in high acetonitrile concentrations. No significant dipeptide synthesis was observed in 25 and 50% acetonitrile; however, reaction rates were similar at acetonitrile concentrations of 75% and above with both producing 24 hour yields of approximately 70%. Longer incubation periods in greater than 90% acetonitrile produced dipeptide yields of greater than 90%. All reactions were run at 40° C.

EXAMPLE 10

Scale-up of Coupling Reaction

A one liter immobilized protease enzyme stirred-tank reactor was used to demonstrate continuous production of Z-aspartyl-L-phenyalanine methyl ester dipeptide. Eighty grams of Amberlite catalyst were placed in 700 ml of neat acetonitrile which contained 160 mM Z-aspartic acid and 480 mM L-phenylalanine methyl ester. The catalyst was prepared as described in Example 1. The reactor temperature was maintained at 40° C. under constant stirring. At the end of 36 hours 90% dipeptide yields were obtained. The reactor was charged with fresh reactants and acetonitrile during three separate operations using the same enzyme catalyst with no loss of activity.

EXAMPLE 11

Synthesis of Z-Asp-L-erythro PhserOMe by Immobilized Pronase in Acetonitrile

To a solution of Z-aspartic acid (192 mg.) and D,L-erythro-phenylserine (411 mg.) in acetonitrile (9 ml.), Pronase E (from Sigma Chemicals) immobilized on Amberlite (1.5 g. wet weight) was added. The mixture was shaken at 23° C. for 19 hours. HPLC analysis indicated that 182 mg. of Z-Asp-L-erythro-PhserOMe was obtained.

EXAMPLE 12

Synthesis of Z-L-Tyr-D-AlaOMe by Immobillized Chymotrypsin in Acetonitrile

To a solution of N-Z-L-tyrosine (102 mg., 0.32 mmol) and D-álanine methyl ester (137 mg., 0.66 mmol) in acetonitrile (4 ml.), chymotrypsin immobilized on Amberlite XAD-7 (0.5 g., wet weight) was added. The mixture was shaken at room temperature for 39 hours. The immobilized enzyme was filtered and the solvent was evaporated to obtain 5 mg. of Z-Tyr-D-AlaOMe.

What is claimed is:

1. In an enzymatic process to cause peptide bond formation between two substrates selected from the group consisting of N-protected aspartic acid of a salt thereof and a phenylalanine lower alkyl ester wherein the benzylic carbon atom is substituted with hydrogen or one or more labile groups readily replaceable with hydrogen, the improvement comprising carrying out said process in a single liquid phase in the presence of a solvent comprising a mixture of acetonitrile and water wherein the weight ratio of acetonitrile to water is greater than 1:1 and in the presence of a water-containing metalloproteinase.

2. A process as in claim 1 wherein the water-containing metalloproteinase is immobilized.

3. A process as in claim 1 wherein the enzyme is thermolysin.

4. A process as in claim 1 wherein the N-protective group is formyl or benzyloxycarbonyl.

5. A process as in claim 1 wherein the phenylalanine benzyl carbon is substituted with hydroxyl.

6. A process as in claim 1 wherein the lower alkyl substituent of the ester is methyl.

7. A process as in claim 1 wherein the process is carried out in the presence of an esterase inhibitor.

8. A process as in claim 1 wherein the N-protective group is tertiary alkoxycarbonyl, benzyloxycarbonyl, p-toluenesulfonyl, o-nitrophenylsulfenyl, or formyl.

9. A process for manufacturing a dipeptide or polypeptide by reacting an acid component of an amino acid or peptide having an N-terminal protective group or a salt thereof with an amine component of an amino acid or peptide having a C-terminal protective group or a salt thereof in a single liquid phase in the presence of a water-containing metalloproteinase and a solvent comprising a mixture of acetonitrile and water wherein the weight ratio of acetonitrile to water is greater than 1:1.

10. A process as in claim 9 wherein the solvent comprises greater than 50 wt.% acetonitrile and the balance is a mixture of water and one or more water-miscible organic solvents.

11. A process as in claim 9 wherein the enzyme is thermolysin.

12. A process as in claim 9 wherein the amino acid having the N-terminal protective group is aspartic acid.

13. A process as in claim 9 wherein the amino acid having the C-terminal protective group is a lower alkyl ester of phenylalanine.

14. A process as in claim 13 wherein the protected amino acid is the methyl ester of phenylalanine.

15. A process as in claim 12 wherein the N-protective group is formyl or benzyloxycarbonyl.

16. A process as in claim 9 wherein an esterase inhibitor is present in the reaction mixture.

17. A process as in claim 9 wherein the N-protective group is tertiary alkoxycarbonyl, benzyloxycarbonyl, p-toluenesulfonyl, o-nitrophenylsulfenyl, or formyl.

18. A process as in claim 1 wherein the phenylalanine lower alkyl ester corresponds to the formula:

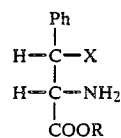

wherein Ph is phenyl, X is —OH, —SH, —Cl, —Br, —I, —PCOCH$_3$, —OCOOCH$_3$, —NH$_2$ or SCH$_3$ and R is an alkyl group having from 1 to 4 carbon atoms.

19. A process as in claim 18 wherein X is —OH and R is methyl.

20. A process as in claim 9 wherein the amino acid having a C-terminal protective group is D-alanine.

21. A process as in claim 1 wherein the enzyme is the protease of Vibrio proteolyticus ATCC 53559.

22. A process as in claim 9 wherein the enzyme is the protease of Vibrio proteolyticus ATCC 53559.

* * * * *